United States Patent

Liaw et al.

[11] Patent Number: 5,844,065
[45] Date of Patent: Dec. 1, 1998

[54] 2,2'-DIMETHYL-4,4'-BIS (4-AMINOPHENOXY) BIPHENYL, AND POLYMERS PREPARED THEREFROM BY POLYCONDENSATION

[75] Inventors: Der-Jang Liaw; Been-Yang Liaw, both of Taipei, Taiwan

[73] Assignee: National Science Council, Taiwan

[21] Appl. No.: 855,969

[22] Filed: May 14, 1997

[51] Int. Cl.⁶ .................... C08G 73/10; C08G 69/26
[52] U.S. Cl. .................... 528/353; 528/125; 528/128; 528/170; 528/172; 528/173; 528/176; 528/183; 528/185; 528/188; 528/220; 528/229; 528/310; 528/322; 528/332; 528/350; 528/352
[58] Field of Search .................... 548/456, 462; 528/170, 125, 128, 172, 173, 176, 183, 185, 188, 220, 229, 310, 322, 332, 350, 353, 352

[56] References Cited

U.S. PATENT DOCUMENTS 4,996,293  2/1991  Tsuyoshi .................... 528/352
5,268,487  12/1993  Yang et al. .................... 548/456
5,414,070  5/1995  Yang et al. .................... 528/353

*Primary Examiner*—P. Hampton-Hightower
*Attorney, Agent, or Firm*—Fish & Richardson, P.C.

[57] ABSTRACT

A new diamine, 2,2'-dimethyl-4,4'-bis(4-aminophenoxy)-biphenyl was synthesized and used to prepare high performance engineering plastics by polycondensation. The new diamine as shown in the following formula has a noncoplanar 2,2'-disubstituted biphenylene and a flexible aryl units:

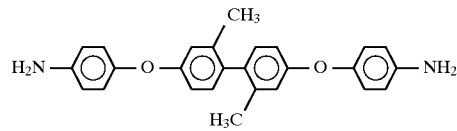

The engineering plastics disclosed in the present invention includes polyamides, polyimides and poly(amide-imide)s.

7 Claims, No Drawings

2,2'-DIMETHYL-4,4'-BIS (4-AMINOPHENOXY) BIPHENYL, AND POLYMERS PREPARED THEREFROM BY POLYCONDENSATION

BACKGROUND

The present invention relates to a new diamine, 2,2'-dimethyl-4,4'-bis(4-aminophenoxy)-biphenyl, and also to polymers polymerized therefrom.

Rod-like aromatic polyamides and polyimides are useful as structural materials with exceptional mechanical and thermal properties. The synthesis and processing of these materials are generally more difficult than those of the conventional flexible-chain polymers due to strong enthalpic interactions and the minimal increase in conformational entropy associated with their dissolution or melting. For example, poly(p-phenyleneterephthalamide) (Kevlar), a well known commercial product and used as a high modulus fiber for a variety of applications is infusible and only soluble in concentrated sulfuric acid. The infusibility and limited solubility of unsubstituted rod-like aromatic polyamides are characteristic properties which restrict synthesis, characterization, processing, and applications, especially of high molecular weight material. Thus, a variety of concepts for structural modifications such as bulky lateral substituents, flexible alkyl side chains, noncoplanar biphenylene moieties, as well as flexible alkyl or aryl ether spacers may be employed to modify the polymer interactions or by reducing the stiffness of the polymer chain. The majority of structure-property investigations on rod-like polymer have been on thermotropic aromatic polyesters and to a smaller extent on aromatic heterocyclic polymers, such as polybenzoxazoles and polybenzthiazoles. Depending on the type and extent of structural modifications, the melting temperatures can be lowered and the solubility improved, resulting in processable materials. To develop high performance polyamides, polyimides and poly(amide-imide), modifications that increase the solubility and lower the transition temperatures while maintaining the rod-like character and thermal stability are of our particular interest.

The present invention synthesizes a new diamine, 2,2'-dimethyl-4,4'-bis(4-aminophenoxy)-biphenyl. The diamine of the present invention as shown in the following formula has a noncoplanar 2,2'-disubstituted biphenylene and a flexible aryl units:

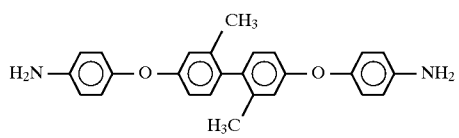

The diamine of the present invention is useful in the preparation of high performance engineering polymers by polycondensation. The incorporation of 2,2'-disubstituted biphenylene in a para-linked polymer chain will not initially change the rod-like structure of the polymer backbone but reduces the interchain interactions. The phenyl rings are forced by the 2,2'-disubstitution into a noncoplanar conformation which decreases the intermolecular forces between the polymer chains. The crystallization tendency and transition temperatures are remarkable lowered and the solubility are significantly enhanced. In addition, the aryl ether linkages inserted in the aromatic main chains provide them with a significantly lower energy of internal rotation, leads to a lower glass transition temperature and crystalline melting temperature as well as significant improvements in solubility and other process characteristics of the polymers without greatly sacrificing thermal stability. According to that mentioned above, introduction of both the noncoplanar 2,2'-disubstituted biphenylene and flexible aryl ether units into polymer backbone would be expected to be a potential structural modifications to the rod-like polymer.

U.S. Pat. Nos. 5268487 and 5414070 disclose an analogous diamine, 3,3'-dimethyl-4,4'-bis(4-aminophenoxy) biphenyl. This diamine does not exhibit the noncoplanar conformation, and thus has less favor polymer processability in comparison with the diamine of the present invention.

SUMMARY

The present invention provides a new diamine, 2,2'-dimethyl-4,4'-bis(4-aminophenoxy)-biphenyl having the following formula:

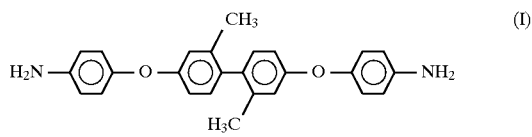

The diamine (I) of the present invention has a noncoplanar 2,2'-disubstituted biphenylene and a flexible aryl units.

The present invention further provides a series of polymers having good heat-resistivity and/or mechanical strength and/or soluble or melting processability, which include polyamides, polyimides and poly(amide-imide)s polycondensated from said diamine (I), 2,2'-dimethyl-4,4'-bis(4-aminophenoxy)biphenyl, and various dicarboxylic acids, various aromatic dianhydrides, trimellitic anhydride and various dicarboxylic acids having the imide ring.

Said polyamides, polyimides and poly(amide-imide)s can be represented by a general formula as follows:

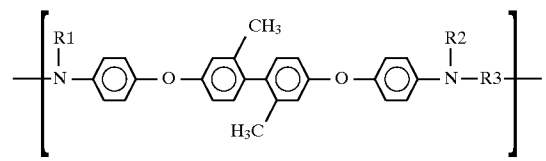

wherein (i) R1 and R2 both are protons (—H), and R3 is:

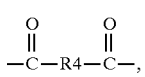

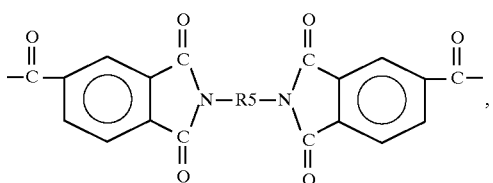

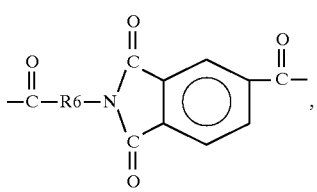

-continued
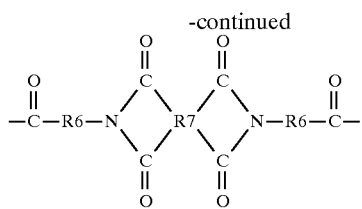
wherein R4 is:
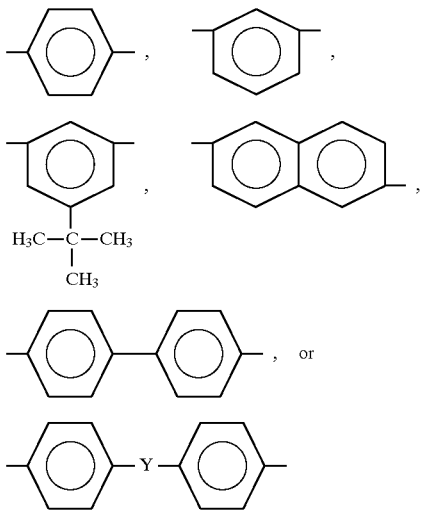
wherein Y=—SO$_2$—, —C(CH$_3$)$_2$—, —C(CF$_3$)$_2$—, or —(CH$_2$)$_m$—,
wherein m is an integer of 2–12,
R5 is:
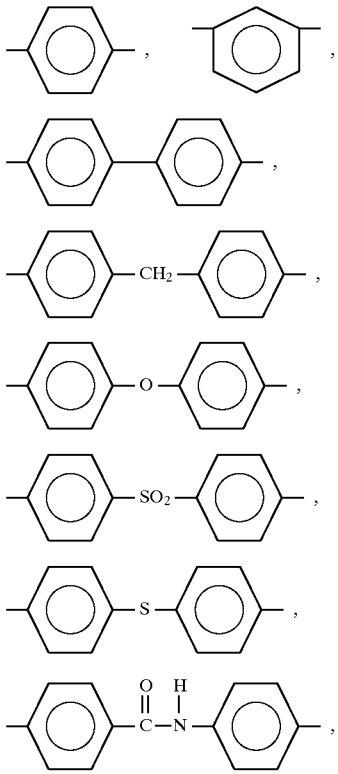
—(CH$_2$)$_m$— (m is the same as above),
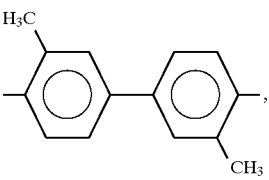
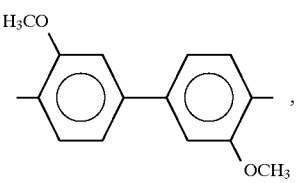
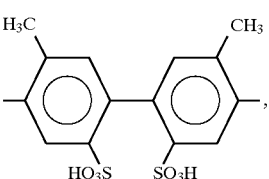
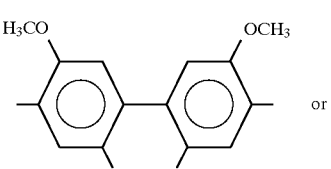
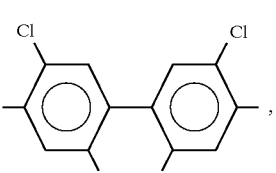
R6 is:
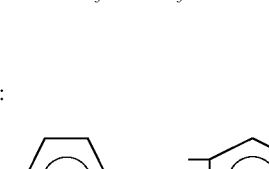
—(CH$_2$)$_n$— (n is an integer of 1–10),
R7 is:
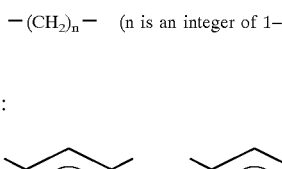

-continued

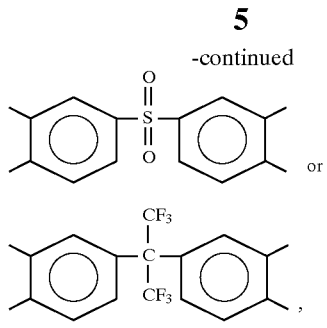 or

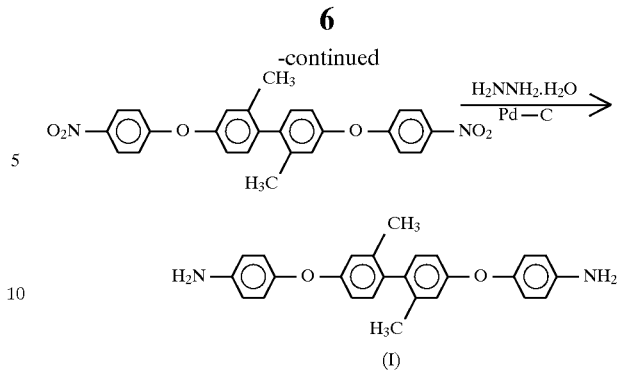

or (ii) R1 and R2 both are not proton (H), R1 represents a single bond, and R2 and R3 cooperatively have the following structure:

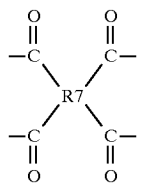

wherein R7 is the same as above.

The polyamide synthesized according to the present invention preferably have an inherent viscosity of 1.03–1.48 dL g$^{-1}$, measured in DMAc (N,N-dimethylacetamide) at a concentration 0.5 g dL$^{-1}$ at 30° C.

The polyimide synthesized according to the present invention preferably have an inherent viscosity of 0.82–1.10 dL g$^{-1}$, measured in concentrated H$_2$SO$_4$ (98%) at a concentration 0.5 g dL$^{-1}$ at 30° C.

DETAILED DESCRIPTION OF THE PREFERRED EMBODIMENTS

The diamine, 2,2'-dimethyl-4,4'-bis(4-aminophenoxy) biphenyl (I), having noncoplanar 2,2'-disubstituted biphenylene and flexible aryl ether units can be condensated from and then reduced by hydrogenation the 2,2'-dimethylbiphenyl-4,4'-diol and the p-chloronitrobenzene. The chemical reaction equation is shown as follows:

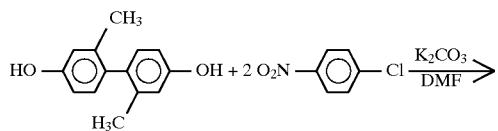

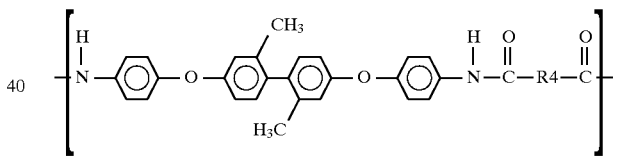

(I)

Polymers prepared by polycondensation from the present diamine (I) include polyamides; polyimides and copoly (amide-imide)s, the preparing methods of which are respectively described in the following text.

The polyamide can be synthesized by polycondensating the diamine (I) with a dicarboxylic acid or an activated dicarboxylic acid. When the diamine (I) is reacted with the dicarboxylic acid, we may use a condensing agent to carry out the polycondensation. One of the most suitable condensing agents is the triphenyl phosphite-pyridine system. When the diamine (I) is reacted with the activated dicarboxylic acid such as the diacid chloride, we may use an aprotic solvent of the amide type such as DMAc or NMP (N-methyl-2-pyrrolidone) to undergo the direct reaction for the manufacture of polyamides. The chemical reaction is shown by the following equation:

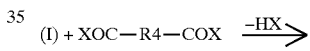

wherein X represents —OH or —Cl, and R4 is as described in the Summary.

The polyimide can be prepared by the polyaddition of the diamine (I) and the dianhydride in the proper organic solvent to form the poly(amic acid). Then the poly(amic acid) is heated or is mixed with a dehydrating agent to form the polyimide. The chemical reactions are shown as follows:

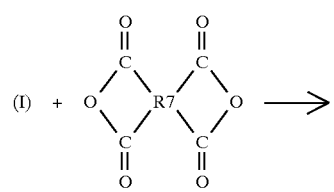

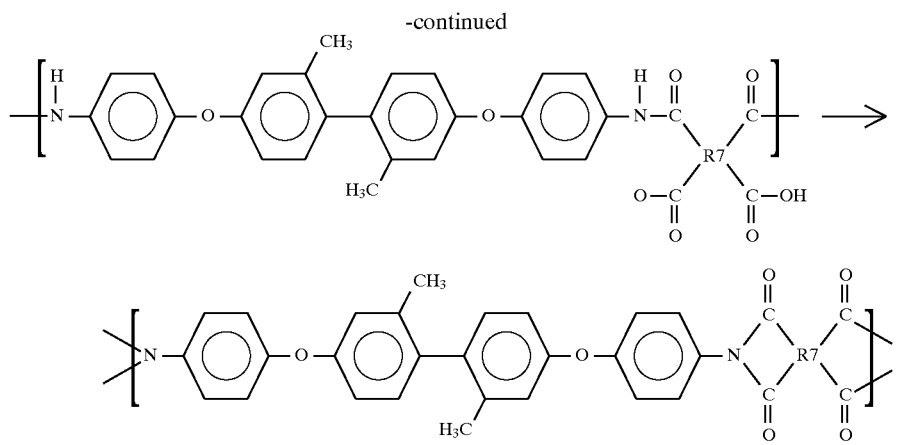

wherein R7 is the same as defined in the Summary.

Trimellitic anhydride (TMA) is used to prepare a copoly(amide-imide). One mole of a diamine and two moles of are condensated to obtain a diimide-diacid which is then polycondensated with the diamine (I) into the copoly(amide-imide) of the alternating type. The chemical reaction equations are as follows:

where R5 is the same as defined in the Summary.

Another type of copoly(amide-imide) may be polycondensated from the diamine (I) and a diimide-diacid condensated from the trimellitic trianhydride (TMA) and an amino acid. The reaction equations are as follows:

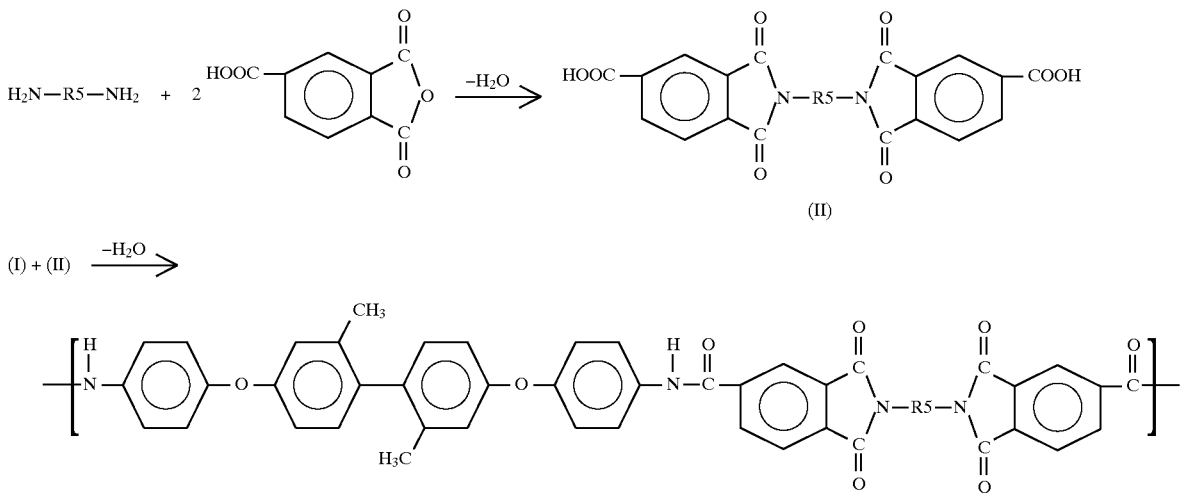

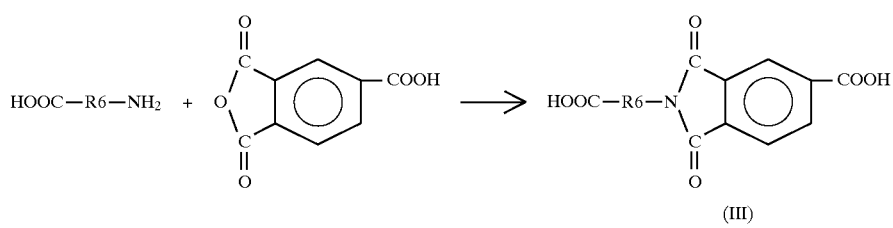

(I) + (III) $\xrightarrow{-H_2O}$ 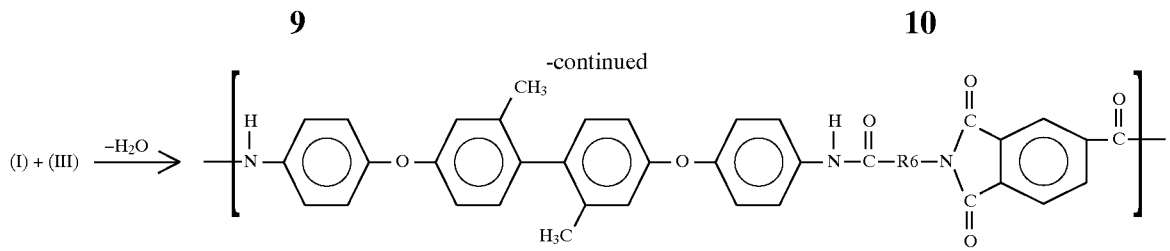

wherein R6 is the same as described in the Summary.

The other type of copoly(amide-imide) can also be synthesized from the diamine (I). It is apparent that a diimide-diacid which is condensated from one mole of a dianhydride and two moles of an amino acid as shown in the following chemical reaction equation is able to be polycondensated with the diamine (I):

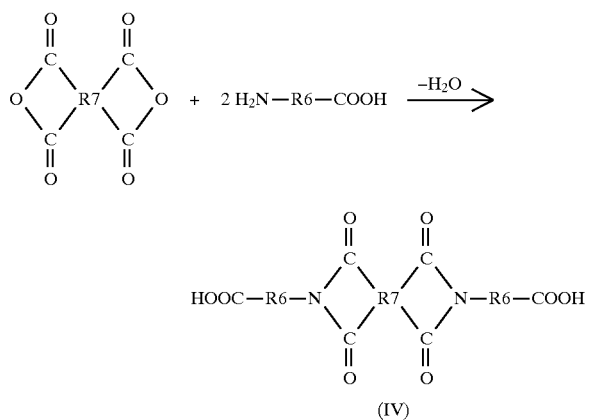

where R6 is as the same as described in the Summary.

Some exemplary processes for preparing the compounds and the polymers according to the present invention are described in details hereinafter.

The preparation of the diamine (I)

A dinitro compound was synthesized by a reaction of 2,2'-dimethylbiphenyl-4,4'-diol[30 g (0.14 mol)] and p-chloronitrobenzene [47.2 g (0.3 mol)] in the presence of potassium carbonate [48.7 g (0.35 mol)] and in DMF (250 mL) at 160° C. for 8 hours. The mixture was then cooled and poured into methanol-water (1:1 by volume). The crude product was recrystallized from glacial acetic acid to provide brown needle (m.p. 142°–144° C.) in 83% yield. The IR spectrum (KBr) exhibited absorption at 1580 and 1339 cm$^{-1}$ (NO$_2$), 1238 cm$^{-1}$ (C—O—C). $^1$H-NMR (CDCl$_3$): δ (ppm) =2.09 (s, 6H), 6.96 (d, 4H), 7.01 (s, 2H), 7.07 (d, 2H), 7.17 (d, 2H), 8.22 (d, 4H). $^{13}$C-NMR (CDCl$_3$): δ (ppm)=19.98, 117.24, 117.53, 121.61, 125.91, 131.15, 137.68, 138.62, 142.72, 154.00, 163.27. Elementary analysis: Calculated values: C, 68.42%; H, 4.39%; N, 6.14%; Analytical values: C, 67.98%; H, 4.59%; N, 6.22%.

45.6 g (0.1 mol) of the resultant dinitro compound, 0.3 g of 10% Pd-C, and 300 mL ethanol were introduced into a three-necked flask to which hydrazine monohydrate (100 mL) was added dropwisely over a period of 0.5 hour at 85° C. Upon completion of the addition, the reaction was continued under reflux for another 24 hours. The mixture was then filtered to remove Pd-C. After cooling, the precipitated crystals were isolated by filtration and recrystallized from ethanol and dried in vacuo. The yield of the diamine was 80%; m.p. 138°–139° C. The IR spectrum (KBr) exhibited absorption at 3324 and 3406 cm$^{-1}$ (N—H), 1226 cm$^{-1}$ (C—O—C). $^1$H-NMR (CDCl$_3$): δ (ppm)=1.94 (s, 6H), 4.99 (s, 4H), 6.62 (d, 4H), 6.69 (d, 2H), 6.78–6.82 (m, 6H), 6.95 (d, 2H). $^{13}$C-NMR (CDCl$_3$): δ (ppm)=19.76, 113.46, 114.89, 117.36, 121.11, 130.57, 134.09, 137.14, 145.43, 145.47, 158.02. Elementary analysis: Calculated values: C, 78.79%; H, 6.06%; N, 7.07%; Analytical values: C, 78.41%; H, 6.34%; N, 7.10%.

The preparation of polyamide

A mixture of 0.495 g (1.25 mmol) of diamine (I), 0.2702 g (1.25 mmol) of 2,6-naphthalenedicarboxylic acid, 0.45 g of calcium chloride, 0.9 mL of triphenyl phosphite, 0.9 mL of pyridine, and 4.5 mL of NMP was heated with stirring at 100° C. for 3 hours. After cooling, the reaction mixture was poured into a methanol bath with constant stirring, producing a stringy precipitate that was washed thoroughly with methanol and hot water, collected on a filter, and dried at 100° C. under vacuum. The inherent viscosity of the polymer is 1.48 dL g$^{-1}$, measured in DMAc at a concentration of 0.5 g dL$^{-1}$ at 30° C. The IR spectrum (film) exhibited absorption at 3280 cm$^{-1}$ (N—H) and 1641 cm$^{-1}$ (C=O). Elementary analysis values, the mechanical strength, the solubility, thermal properties and the molecular structure thereof are shown as follows:

Elementary Analysis: (C$_{38}$H$_{28}$N$_2$O$_4$)$_n$ calculated values: C, 79.15%; H, 4.89%; N, 4.86%; analytical values: C, 76.10%; H, 5.18%; N, 4.73% (with moisture absorption 3.6%); revised values: C, 78.91%; H, 5.00%; N, 4.90%.

Mechanical Properties:

| Tensile Strength (MPa) | Elongation at Break (%) | Initial Modulus (GPa) |
|---|---|---|
| 40 | 3 | 1.42 |

Solubility[a]:

| | | | Solvent[b] | | | |
|---|---|---|---|---|---|---|
| NMP | DMSO | DMAc | DMF | m-cresol | Py | THF |
| + | + | + | + | + | + | + − |

Thermal Properties:

| Melting temperature (°C.) | 10% weight loss Temperature in nitrogen (°C.) | Char Yield in nitrogen at 800° C. (%) |
|---|---|---|
| 392 | 496 | 61 |

Molecular Structure:

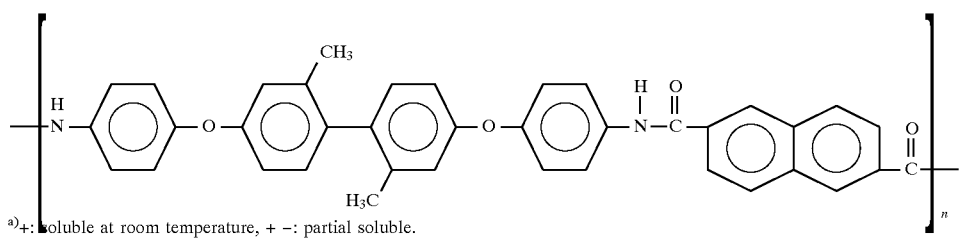

[a]+: soluble at room temperature, + −: partial soluble.
[b]NMP: N-methyl-2-pyrrolidone; DMSO: dimethylsulfoxide; DMAc: N,N-dimethylacetamide; DMF: dimethylformamide; Py: pyridine; THF: tetrahydrofuran The value of n in the polymer structure can be determined from the molecular weight and molecular weight distribution obtained by size-exclusion chromatography (GPC) measurement.

The preparation of the polyimide

To a stirred solution of 0.495 g (1.25 mmol) diamine (I) in 8 mL anhydrous DMAc was added gradually 0.4025 g (1.25 mmol) of 3,3',4,4'-benzophenonetetracarboxylic dianhydride (BTDA). The mixture was stirred at room temperature for 2 hours under argon atmosphere. The inherent viscosity of the poly(amic acid) was 2.01 dL g$^{-1}$, measured in DMAc at a concentration of 0.5 g dL$^{-1}$ at 30° C. The poly(amic acid) was cast on a clean glass plate which was then put into an oven to be baked at 80° C. to form a solid film through evaporation of the solvent, and was further baked in the oven at 110, 150, 180, 210, 230, and 250° C. for 20 minutes at each temperature. A polyimide thin film was thus obtained. The inherent viscosity of the polyimide was 0.90 dL g$^{-1}$, measured in concentrated H$_2$SO$_4$ (98%) at a concentration of 0.5 g dL$^{-1}$ at 30° C. The elementary analysis values, the mechanical strength, thermal properties, and molecular structure are listed as follows:

Elementary Analysis: $(C_{43}H_{26}N_2O_3)_n$ Calculated values: C, 75.60%; H, 3.81%; N, 4.10%; Analytical values: C, 74.14%; H, 3.90%; N, 4.02%.

Mechanical Properties:

| Tensile Strength (MPa) | Elongation at Break (%) | Initial Modulus (GPa) |
|---|---|---|
| 139 | 8 | 1.81 |

Thermal properties:

Melting temperature: 336° C.;
Glass transition temperature: 256° C.

Molecular Structure:

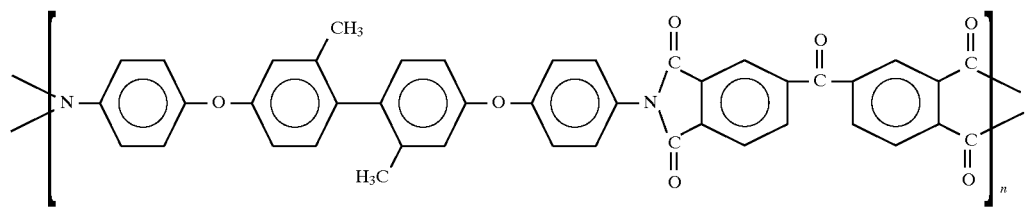

The value of n in the polymer structure can be determined from the molecular weight and molecular weight distribution obtained by size-exclusion chromatography (GPC) measurement.

The poly(amide-imide)s can be prepared by the procedures which are similar to those of the preparation of polyamide and polyimide. These poly(amide-imide)s also exhibit good mechanical properties and/or thermal stability and/or soluble or melting processability.

What we claim is:

1. An aromatic polyimide polymer having the following structure:

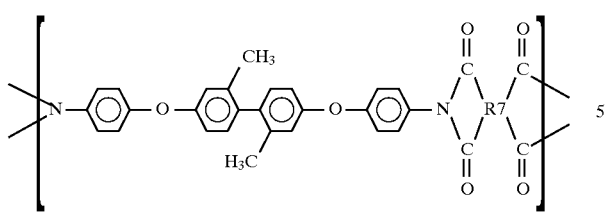

wherein R7 is selected from the group consisting of

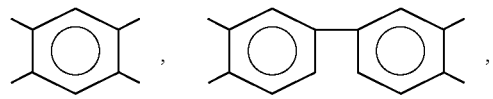

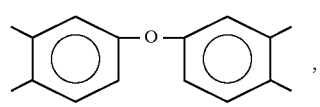

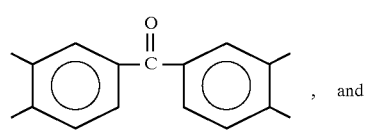, and

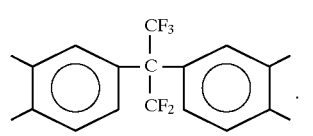

2. The polymer according to claim 1, wherein said polymer has an inherent viscosity of 0.82–1.10 dL g$^{-1}$, measured in concentrated H$_2$SO$_4$ (98%) at a concentration 0.5 g dL$^{-1}$ at 30° C.

3. The polymer according to claim 1, wherein said R7 is

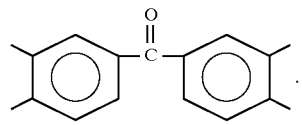

4. An aromatic polyamide having the following structure:

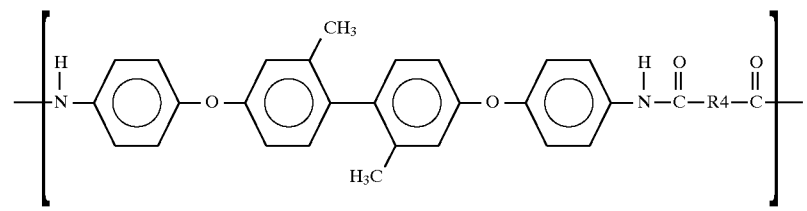

wherein R4 is:

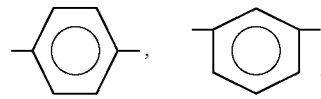

-continued

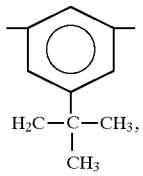

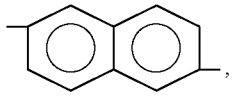

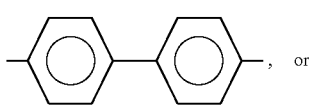, or

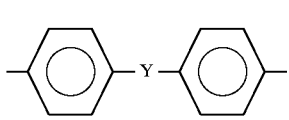

wherein Y=—SO$_2$—, —C(CH$_3$)$_2$—, —C(CF$_3$)$_2$—, or —(CH$_2$)$_m$—, wherein m is an integer of 2–12.

5. The polymer according to claim 4, wherein said polymer has an inherent viscosity of 1.03–1.48 dL g$^{-1}$, measured in N,N-dimethylacetamide (DMAc) at a concentration 0.5 g dL$^{-1}$ at 30° C.

6. The polymer according to claim 4, wherein said R4 is

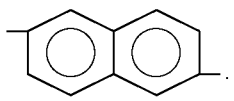

7. An aromatic poly(amide-imide) having the following structure:

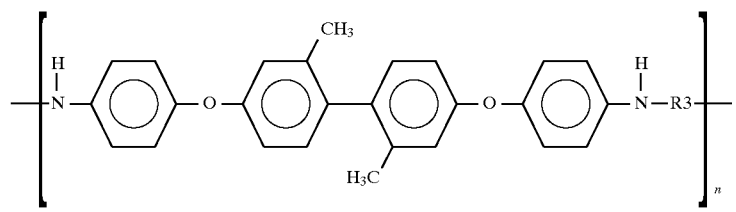
wherein R3 is selected from the group consisting of
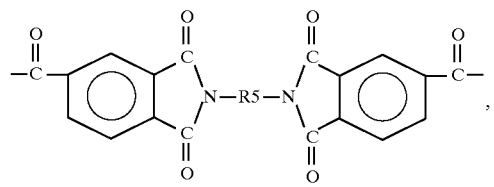
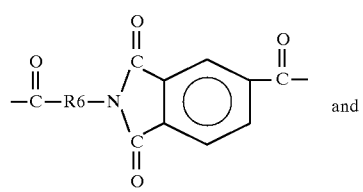
,
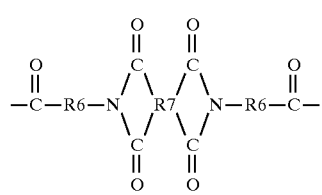
wherein R5 is selected from the group consisting of
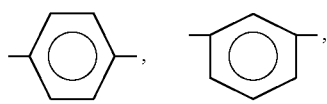
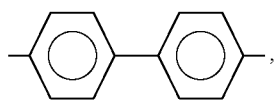
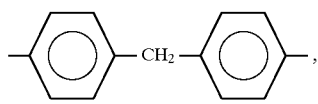
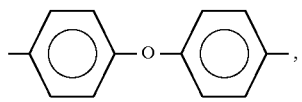
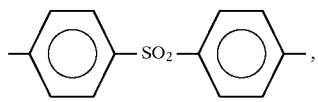
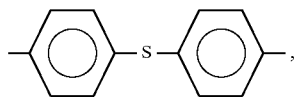
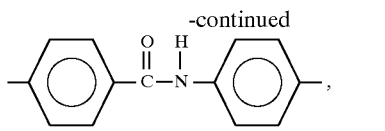
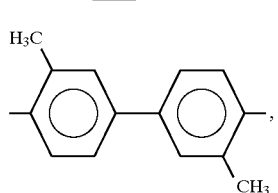
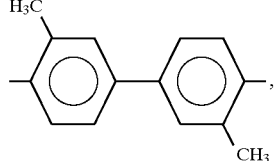
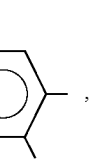
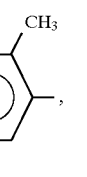
and
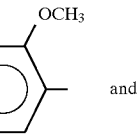
wherein m is an integer from about 2 to about 12
R6 is selected from the group consisting of
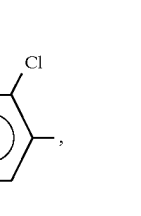
wherein n is an integer of 1–10; and R7 is selected from the group consisting of
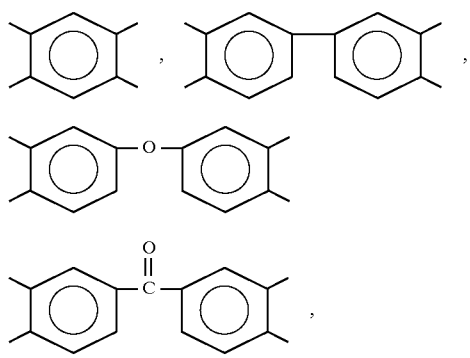,
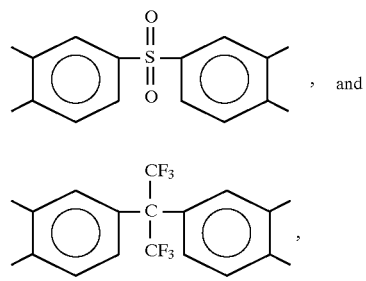, and